United States Patent [19]

Stamm

[11] 3,956,695

[45] May 11, 1976

[54] MICROWAVE SPECTRAL IDENTIFICATION OF CELLS

[76] Inventor: Michael E. Stamm, 10965 Rochester No. 104, Los Angeles, Calif. 90024

[22] Filed: July 22, 1974

[21] Appl. No.: 490,260

[52] U.S. Cl. ............................................ 324/58.5 A
[51] Int. Cl.² ........................................ G01R 27/04
[58] Field of Search .............................. 324/58.5 A

[56] References Cited
UNITED STATES PATENTS

| | | | |
|---|---|---|---|
| 2,532,817 | 12/1950 | Lafferty et al. ................. | 324/58.5 A |
| 3,034,046 | 5/1962 | Sasaki ............................ | 324/58.5 A |
| 3,107,329 | 10/1963 | McSkimin et al. ........... | 324/58.5 A X |
| 3,265,967 | 8/1966 | Heald ............................. | 324/58.5 A |
| 3,439,266 | 4/1969 | Rogers ........................... | 324/58.5 A |
| 3,711,769 | 1/1973 | Peake ............................. | 324/58 A |
| 3,866,118 | 2/1975 | Ghosh et al. ................... | 324/58.5 A |

Primary Examiner—Stanley T. Krawczewicz
Attorney, Agent, or Firm—Edwin A. Oser

[57] ABSTRACT

The nature of cells such as human or animal cells is identified by means of microwaves. The cells to be identified, as well as normal cells, are interposed respectively into one of two microwave beams thereby to obtain microwave absorption spectra. The two spectra are subtracted from each other preferably by shifting the phase of one beam by 180° so that the two microwave spectra normally cancel each other. The resultant spectrum is detected and may be recorded, or otherwise exhibited by an oscilloscope. Instead of using cells, it is possible to use tissues or slices. It has been found that the thus obtained microwave spectra are characteristic of malignant cells and permit to distinguish, for example, between carcinomas, sarcomas and melanomas. The microwave range may be between 5 and 150 GHz (gigahertz) and preferably the range is between 76 to 86 GHz.

4 Claims, 5 Drawing Figures

MICROWAVE SPECTRAL IDENTIFICATION OF CELLS

BACKGROUND OF THE INVENTION

This invention relates generally to microwave spectroscopy, and particularly relates to a method of and apparatus for identifying the nature of cells such as malignant cells.

Some time ago it was discovered that the microwave absorption of normal and tumorous or malignant cells differs. This has been pointed out by a paper by Webb and Booth entitled "Microwave Absorption by Normal and Tumor Cells" which appears in *Science*, Vol. 174, October 1, 1971, pages 72–74. In this paper, the microwave absorption of cells or tissues has been measured at various discrete frequencies by a Klystron. The frequency range from 66 to 76 GHz was used. Each set of cells was measured separately and the results were subtracted from each other.

Due to the fact that separate measurements had to be made at different frequencies, it is difficult to compare the measurements with each other. It is equally difficult or laborious to subtract the attenuation obtained from one set of cells from that of another. Therefore, the so called base line could not be established with any degree of certainty. That is, it is not certain whether results obtained at one frequency are comparable to those obtained at another frequency. For these reasons, the method disclosed in the Webb et al. paper could not be used for identifying a particular type of cell or distinguishing it from normal cells.

It is frequently desired to determine the nature of tissues taken from a patient during an operation. In this case, a long waiting period can often not be tolerated because the surgeon cannot wait an indefinite period of time until finishing the operation. Even with modern methods it may take an appreciable time to obtain an analysis whether the tissue is cancerous or not with any degree of certainty.

In some cases the specimen taken from a patient may have to be prepared for subsequent culture using sterile procedures. In this case, the tissue may have to be grown and passed through several passages before it can be analyzed. As a result, it is possible that the tissue materially changes its nature before it can be analyzed. For example, if the original tissue showed a certain degree of malignancy, the tissue, after several passages, may show nothing but malignant cells, or it may even show nothing but normal cells. Thus, the serially passed culture may have cells which change their morphologic appearance and, therefore, an absolute identification may not be possible.

It is accordingly an object of the present invention to provide a method of and apparatus for identifying the nature of cells which can be effected rapidly and without the need to grow cells over various passages.

A further object of the present invention is to provide a microwave analysis of cells which can be rapidly carried out and which positively identifies various types of malignancy, such as, for example, carcinoma, sarcoma and melanoma.

Still another object of the present invention is to provide a system of the type discussed which will permit the simultaneous comparison of normal cells with malignant cells, both being autologous cells.

SUMMARY OF THE INVENTION

In accordance with the present invention, there is provided an apparatus for identifying the nature of cells by simultaneously comparing them with normal cells. The word "cells" is meant to include tissues, which are, of course, nothing but a large number of cells. The apparatus comprises a microwave generator which includes means for varying its frequency over a predetermined range to develop an output wave. Therefore, the frequency of the output wave varies continuously. The frequency range may be from approximately 5 to approximately 150 GHz and preferably from approximately 76 to approximately 86 GHz.

Means are provided for splitting the output wave of the generator into two spatially separated beams. Means are disposed respectively in the path of each beam for interposing normal cells and the cells to be identified. Further means are provided for subtracting the microwave radiation having passed through one of the cells from the radiation having passed through the other cells. This may be conveniently effected by shifting the phase of one of the beams by 180°. Finally, a microwave detector is provided for detecting the difference of the microwave radiation having passed through both of the cells. As a result, the nature of the cells to be identified can now be determined. Preferably, the two sets of cells are autologous cells, that is, originated from the same patient.

The novel features that are considered characteristic of this invention are set forth with particularity in the appended claims. The invention itself, however, both as to its organization and method of operation, as well as additional objects and advantages thereof, will best be understood from the following description when read in connection with the accompanying drawings.

DESCRIPTION OF THE PREFERRED EMBODIMENT

Figure 1:
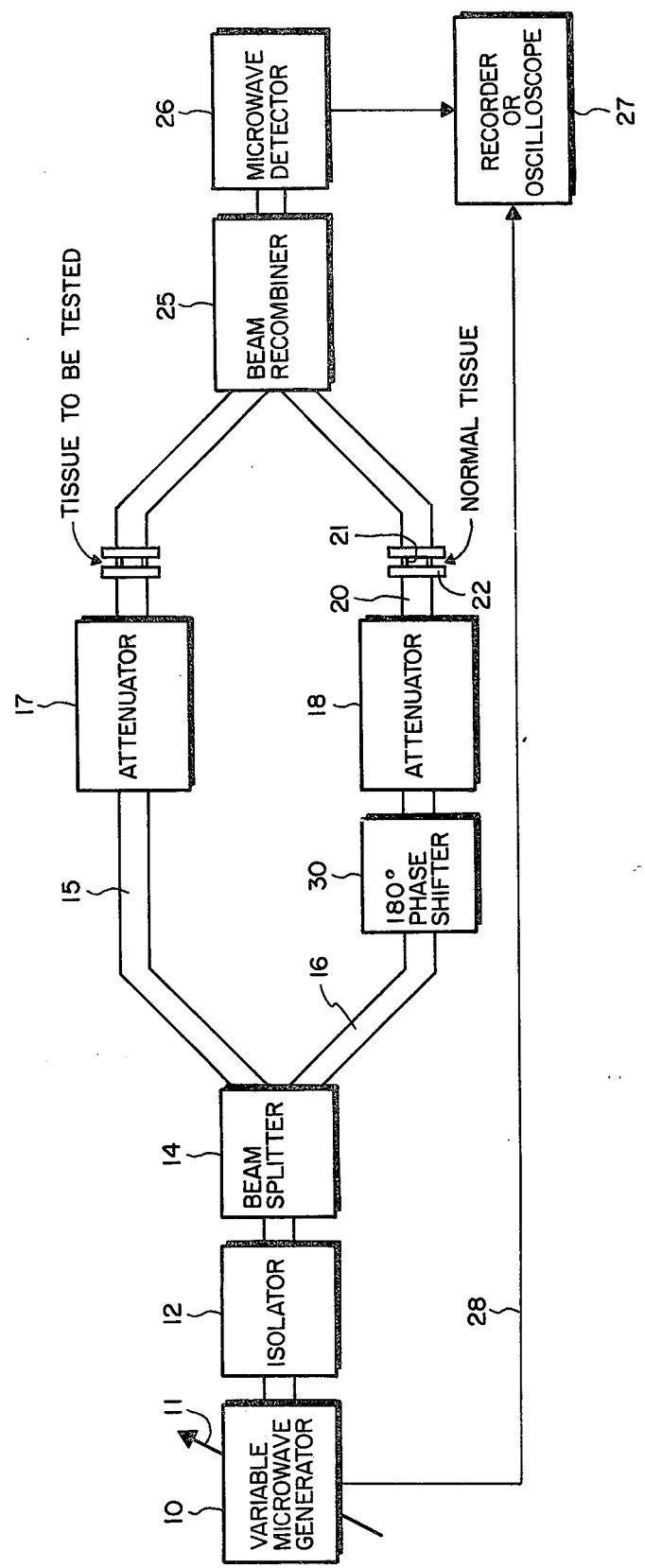
FIG. 1 is a schematic view in block form of an apparatus embodying the present invention.

Referring now to FIG. 1, there is illustrated in block form an apparatus embodying the present invention. The apparatus of FIG. 1 includes a variable microwave generator 10. The microwave generator 10 is continuously variable over a predetermined frequency range as indicated by the arrow 11. Such microwave generators are readily obtainable in the trade. For example, Model No. 440XXH represents a series of microwave generators obtainable from Hughes Aircraft Company. By way of example, Model No. 44076H is a millimeter wave generator having a 3 mW output over a 10 GHz bandwidth between 60 to 90 GHz and includes an isolator. Other models are available with other frequency ranges and with similar power outputs. Preferably, an isolator 12 follows the microwave generator 10 to stabilize the oscillator and to isolate it from its output.

The isolator 12 is followed by a beamsplitter 14. The beamsplitter 14 may consist of a conventional stripline or waveguide. Such beamsplitters and waveguides are well known in the art and are also obtainable from Hughes Aircraft Company.

As a result, two beams, 15 and 16, are now obtained which have substantially equal power. The beams may be guided, for example, by a millimeter transmission line such as a waveguide or stripline. In order to insure that the two beams have exactly equal power, an attenuator 17 may be disposed in the waveguide 15 and another attenuator 18 in the waveguide 16.

The attenuators may simply consist of a waveguide section into which a graphite rod may be lowered. Depending on the position of the rod, the graphite will absorb more or less of the energy of the two beams, thereby to permit a precise adjustment of the power of the two beams.

A normal tissue may be inserted into a waveguide section 20. To this end, the waveguide section 20 may be provided with an aperture 21 at the top thereof, and the tissue or cell may be guided by a pair of flanges 22 extending from the waveguide section. A similar structure or tissue holder 23 is disposed in the waveguide section 24 of the other beam to insert therein the tissue or cells to be tested.

The two beams are now recombined by a beam recombiner 25 which may simply be the reverse of beamsplitter 14 and the beam recombiner is followed by a microwave detector 26. The microwave detector 26 is preferably a broadband crystal detector. Such detectors are readily available in the trade such as Model No. 44809H which is obtainable from Hughes Aircraft Company. This detector will detect microwaves within a 10 GHz band between 60 to 90 GHz. Other detectors are available in this series for other microwave bands.

The microwave detector 26 may be followed by a recorder 27 for recording the microwave spectra. Alternatively, an oscilloscope may be used and the trace photographed to obtain the spectrum. The recorder or oscilloscope 27 may be coupled to the generator 10 as indicated by the lead 28. This will insure that the recorder or oscilloscope will sweep in synchronism with the sweep of the oscillator 10.

In order to subtract the two microwave absorption spectra from each other there may be conveniently provided a 180° phase shifter 30 which may be interposed into the path of either beams 15 or 16. It is shown interposed into the path of beam 16. The phase shifter should be so adjusted that no output is detected by the microwave detector 26 in the absence of any tissue or cells inserted into the tissue holder 21, 22 or 23.

Before explaining the operation of the apparatus of FIG. 1, it will be convenient at this point to explain how the cell specimens may be obtained. Thus, for example, fresh tumor specimens and normal control tissues may be obtained from the cancer patient at the time of surgery. These, of course, are autologous cells which are preferably used for the method of the invention. These specimens are tissues separately prepared for culture using sterile procedures. The tissues are finely minced, for example, with scissors, washed and planted into a suitable growth medium. Cells at the second passage level from these tissue cultures may be used.

The samples are removed by pipet after scraping a small area of the flask wall. Approximately 1 to 3 million cells are removed. The cells are then centrifuged at 1000 g for eight minutes to form a pellet. A small portion of the pellet is placed on a piece of plastic, such, for example, a sheet of mylar having a thickness of ¼ mil. The mylar is folded to contain the sample and the cells are spread by capillary attraction to form a sheet of approximately uniform thickness which may be 0.07 mil thick. It should be noted that sterile techniques are observed throughout the entire procedure. The cells in the folded mylar envelope are then inserted respectively into the tissue holders 21, 22 and 23. The flanges 22 will firmly hold the mylar envelope.

The apparatus of FIG. 1 operates in the following manner. The two attenuators 17 and 18 are first carefully adjusted to obtain zero output at the detector 26. At the same time, the 180° phase shifter 30 insures that the two beams will subtract each other or cancel each other at the detector 26. Subsequently, the normal tissue is inserted into the beam 16 and the tissue to be tested is inserted into the beam 15. When the generator 10 is swept through its frequency range, the differential absorption spectrum is detected by the detector 26 and may be recorded by the recorder 27 or exhibited by the oscilloscope.

Some of the microwave absorption spectra which have been obtained with the apparatus of FIG. 1, are shown in FIGS. 2 through 5 which will now be discussed.

Figure 2:
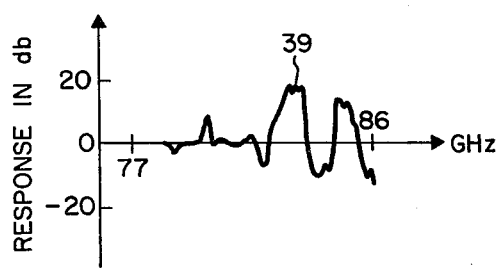
FIGS. 2 and 3 are microwave spectra plotting the frequency as a function of the response for two different patients having breast carcinoma.
Figure 3:
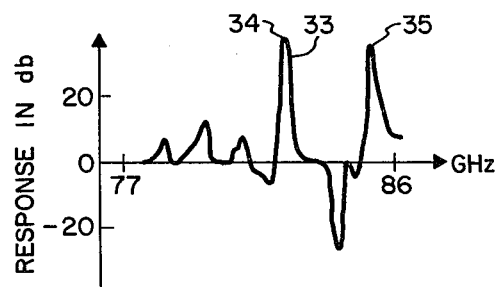

FIG. 2 shows a differential microwave spectrum 32 in the frequency range from 77 to 86 GHz. The differential response in db is shown. FIG. 2 is the differential absorption spectrum of tissue from a patient suffering from breast carcinoma. FIG. 3 shows a similar curve 33 taken over the same frequency range. This specimen was also taken from a patient having breast carcinoma. It will be noted that the two responses are quite similar, so that it is possible to determine the nature of the malignancy from the type of microwave spectrum obtained. It should also be noted that the amplitude of the response such as the peaks 34 and 35 of the spectrum 33 of FIG. 3 are an indication of the amount of tumorous cells compared to normal cells in the tissue sample. Thus, if both beams were transmitted through normal cells, there should be a zero response. If, on the other hand, the tissue to be tested contains half tumor and half normal cells, then the energy at the detector represents half the amplitude of the differential absorption spectrum. Thus, the sample from the patient of FIG. 3 obviously contains more tumorous cells than that of FIG. 2.

Figure 4:
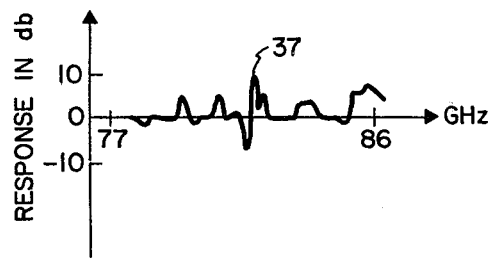
FIGS. 4 and 5 are charts similar to those of FIGS. 2 and 3 plotting the frequency as a function of the response for two different patients having melanoma.
Figure 5:
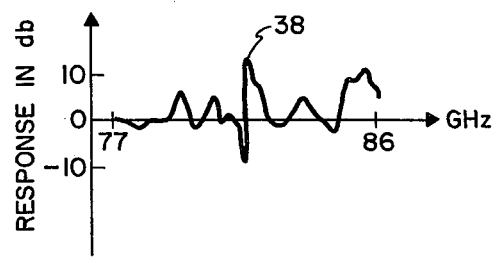

FIGS. 4 and 5, to which reference is now made, show microwave absorption spectra 37 and 38, both corresponding to a frequency range from 77 to 86 GHz. The response is again given in db. The spectra 37 and 38 were obtained from tissues of two different patients, each suffering from melanoma. It should be noted that for the charts of FIGS. 2 through 5 the response of the malignant tissues was subtracted from that of the normal cells. It will also be noted that the sharpness of the response, such as that of curve 33 or 37, is also an indication of the ratio of malignant to normal cells.

It is believed that malignant cells have a different absorption spectrum because the DNA (deoxyribonucleic acid) of a malignant cell is different from that of a normal cell. It is also well known that the nucleus of a malignant cell or cancer cell is larger than that of a normal cell which is again due to the difference of the respective DNA.

There has thus been disclosed an apparatus for and method of identifying the nature of cells. Malignant cells are compared to normal cells by subtracting their microwave spectra. This is effected conveniently by shifting the phase through 180° of one of the two beams. The frequency of the generator is continuously varied over a predetermined range. The resulting differential absorption spectra make it possible to draw conclusions not only whether the cells are malignant, but of the particular type of malignancy, such, for example, as carcinoma, sarcoma and melanoma.

What is claimed is:

1. The method of automatically determining possible malignancy in cells to be tested by microwave spectral analysis by subtracting the spectrum of normal cells from that of cells to be tested, said method comprising the steps of:
   a. generating a first microwave beam;
   b. generating a second microwave beam of substantially equal phase, frequency and power;
   c. spreading normal cells into a thin, substantially uniform layer;
   d. interposing the layer of the normal cells into the path of the first beam;
   e. spreading cells to be tested into a thin, substantially uniform layer;
   f. interposing the layer of cells to be tested into the path of the second beam;
   g. shifting the phase of one of the beams by 180°;
   h. varying the frequency of the microwave beams simultaneously over a predetermined frequency range; and
   i. detecting the difference of the response of the two beams over the predetermined frequency range, whereby the spectrum of the normal cells is automatically subtracted from the spectrum of the cells to be tested over the predetermined frequency range to determine the presence of malignancy.

2. The method defined in claim 1 which includes the additional step of recording the differential response obtained from the detecting step.

3. The method defined in claim 1 wherein the normal cells and the cells to be identified consist each of a slice of tissue.

4. The method defined in claim 1 wherein the normal cells and the cells to be identified are autologous cells.

* * * * *